US00PP21281P3

(12) United States Plant Patent
Lowe

(10) Patent No.: US PP21,281 P3
(45) Date of Patent: Sep. 7, 2010

(54) ***DIANELLA PRUNINA* PLANT NAMED 'DPV308'**

(50) Latin Name: *Dianella prunina*
Varietal Denomination: DPV308

(76) Inventor: Greg Lowe, 202 Tumbi Rd., Tumbi Umbi NSW (AU) 2261

( * ) Notice: Subject to any disclaimer, the term of this patent is extended or adjusted under 35 U.S.C. 154(b) by 0 days.

(21) Appl. No.: 12/386,721

(22) Filed: Apr. 23, 2009

(65) Prior Publication Data

US 2009/0307815 P1 Dec. 10, 2009

(51) Int. Cl.
*A01H 5/00* (2006.01)

(52) U.S. Cl. ..... Plt./424

(58) Field of Classification Search ..... Plt./424
See application file for complete search history.

*Primary Examiner*—Annette H Para

(57) ABSTRACT

'DPV308' is a distinctive variety of *Dianella prunina,* which is characterized by its combination of leaf variegation, short plant height short internodes and an absence of aerial stems and erect and compact plant growth habit with medium density of shoots suited to potted and landscape growing conditions and ease of vegetative propagation by division and micropropagation.

4 Drawing Sheets

Latin name of the genus and species: The Latin name of the novel variety disclosed herein is *Dianella prunina.*

Variety denomination: The inventive variety of *Dianella prunina* disclosed herein has been given the variety denomination 'DPV308'.

BACKGROUND OF THE INVENTION

The present invention relates to a new and distinct variety of evergreen perennial *Dianella prunina,* which has been named 'DPV308'. *Dianella* are a genus of ornamental grass-like plants. *Dianella prunina* has flax-like leaves.

An application for plant breeders' rights for 'DPV308' has been lodged with the Australian Plant Breeders Rights Office, and was filed on Jun. 10 2008 (under Application No. 2008/180).

Parentage: The cultivar 'DPV308' was discovered in 2006 in Tumbi Umbi, New South Wales, Australia, as a spontaneous mutation of in vitro cultivated *Dianella prunina* 'DP303' (U.S. provisional application No. 60/761,135). The parent form is characterized by a short plant height, and an absence of leaf variegation. Selection criterion for 'DPV308' was presence of leaf variegation. It was subsequently found to have a short plant height and compact plant growth habit suited to potted and landscape growing conditions as well as an ease of vegetative propagation by micropropagation and division.

Asexual reproduction. The new variety 'DPV308' was first asexually propagated by vegetative micropropagation in the state of New South Wales, Australia in October 2006 and has been asexually propagated since that time by division and micropropagation. The distinctive characteristics of cultivar 'DPV308' have remained stable and true to type through successive cycles of asexual propagation.

SUMMARY OF THE INVENTION

'DPV308' is a distinctive variety of *Dianella prunina,* which is characterized by its combination of leaf variegation, short plant height and compact plant growth habit suited to potted and landscape growing conditions and ease of vegetative propagation by division and micropropagation.

DETAILED BOTANICAL DESCRIPTION OF THE VARIETY

Figure 1:
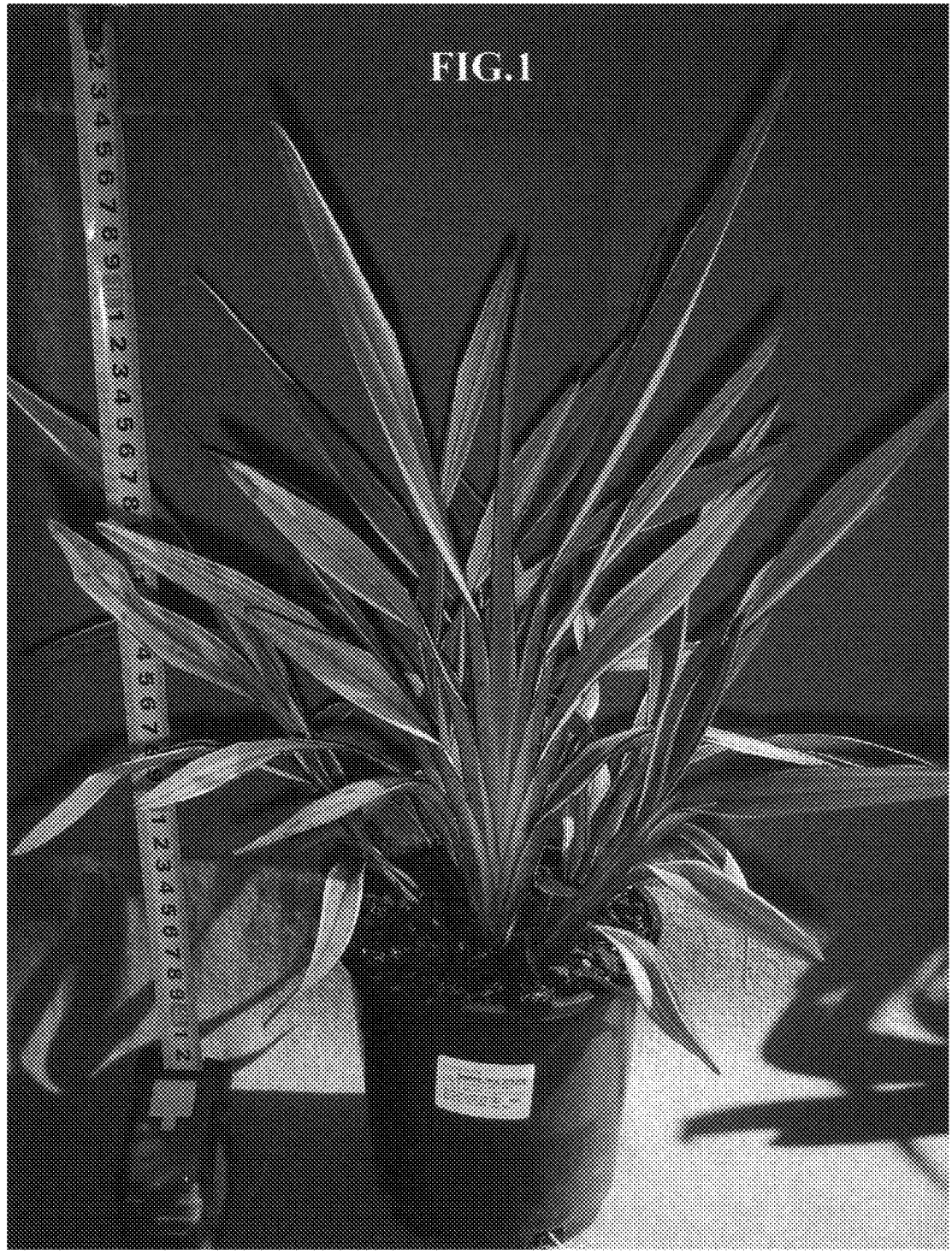
FIG. 1 shows an exemplary *Dianella prunina* 'DPV308' plant at approximately 8-months of age growing in a 140 mm pot. The plant was propagated in a greenhouse and was transferred to the field at four months and grown out in full sun for the final four months.

The following is a detailed botanical description of a new and distinct variety of *Dianella prunina* known as 'DPV308' based upon observations of 8-month old plants grown in 140 mm nursery pots in full sun in open beds in Clarendon, New South Wales, Australia during summer to autumn 2009. Plant observations and descriptions were taken in summer 2008 and again in autumn 2009.

Those skilled in the art will appreciate that certain characteristics will vary with older or, conversely, with younger plants. 'DPV308' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

'DPV308' is an evergreen perennial *Dianella prunina.* 'DPV308' is a compact, erect plant with medium density plant growth habit, short internodes and an absence of aerial stems, short plant height including foliage, medium leaf blade widths with a variegated leaf coloration and strong leaf glaucosity giving an overall grayish green foliar appearance with contrasting grayed purple and yellow white variegation. These characteristics are unusual for *Dianella prunina,* as these plants do not have a leaf variegation and usually have a sparse shoot density, tall plant height and wider leaves than 'DPV308'. 'DPV308' has not produced any flowers to date. Botanical description of 'DPV308' and comparisons with the parent 'DP303' are provided below.

Technical Description of the Variety

Plant characteristics: Growth habit erect, height short (mean 30.0 cm), medium density of shoots with very short internodes (to 10 mm) and an absence of aerial stems.

Leaves: Attitude erect to semi-erect, width medium (mean 15.0 mm); variegation present; upper side predominant color yellow green (RHS 147A) with surface waxiness removed and grayed green (RHS 189A) with surface waxiness retained. This predominant color has fine striations running parallel to the venation which approximate to color grayed green (RHS N189D); the variegation consists of a prominent extreme marginal color grayed purple (RHS 185 A-B) of width approximately 1 mm from leaf base to apex. Inside the marginal color is a secondary variegation of color yellow white (RHS 158A-B) of width 1 mm to 2 mm. The upper side mid rib coloration is the same as the predominant upper side leaf grayed green (RHS 189A) color and does not significantly contrast to the leaf.

The lower side color is the same as the upper side with the exception of the mid rib which has a contrasting color grayed purple (RHS 185 A). Lower side mid rib spines present with weak prominence.

Leaf blade shape is ligulate, apex apiculate, base is cauline, cross section concave with blade recurving toward margin, margin is entire. Arching of leaf blade is present, predominantly in outer leaves of a shoot. Leaf blade twisting is present with weak to medium prominence.

Basal sheath: Sheath margin has prominent variegation with the margin contrasting to the remainder of the sheath; marginal coloration is approximately 3 mm wide at base and gradually reduces to meet the marginal width of the leaf variegation. Margin and midrib color are grayed purple (RHS 185A-B), and prominent, Remainder of sheath is colored grayed green (RHS N189D); mid rib coloration of sheath has width of approximately 1 mm. Sheath length range 6 to 10 cm, margin is entire.

Basal Shoots: Attitude erect, arrangement a cluster, cross-sectional profile is flat density is medium with approximately 9 shoots produced on an 8 month old plant grown in a 140 mm pot in a soil-less potting medium in Clarendon, NSW Australia from spring 2008 to autumn 2009.

Flowers and berries: 'DPV308' has not flowered to date.

Cold and Heat Tolerance: 'DPV308' has been observed to be cold tolerant to −5° C. in Australia. Foliage color did not change under these conditions, except for a slight burning at the very tips of the leaves. The plant has also been grown for one year in Charleston, S.C., USA and has remained evergreen down to −6° C.

'DPV308' is also very heat tolerant. It adapted well to the high heat conditions during summer in Clarendon, New South Wales, Australia and high heat conditions during summer in Charleston, S.C., USA without any noticeable disease or insect damage.

Drought tolerance: Very good drought tolerance; 'DPV308' survived three months without rainfall under hot conditions in non-irrigated garden beds in Clarendon, Australia in Summer, 2008-2009.

Pest Resistance: No known pests.

Cultural conditions: 'DPV308' can tolerate low nutrient conditions; it does not like continually wet soil conditions, but can tolerate well-draining sandy soils to very heavy clay soils. pH characteristics of the variety are fairly adaptable.

Figure 2:
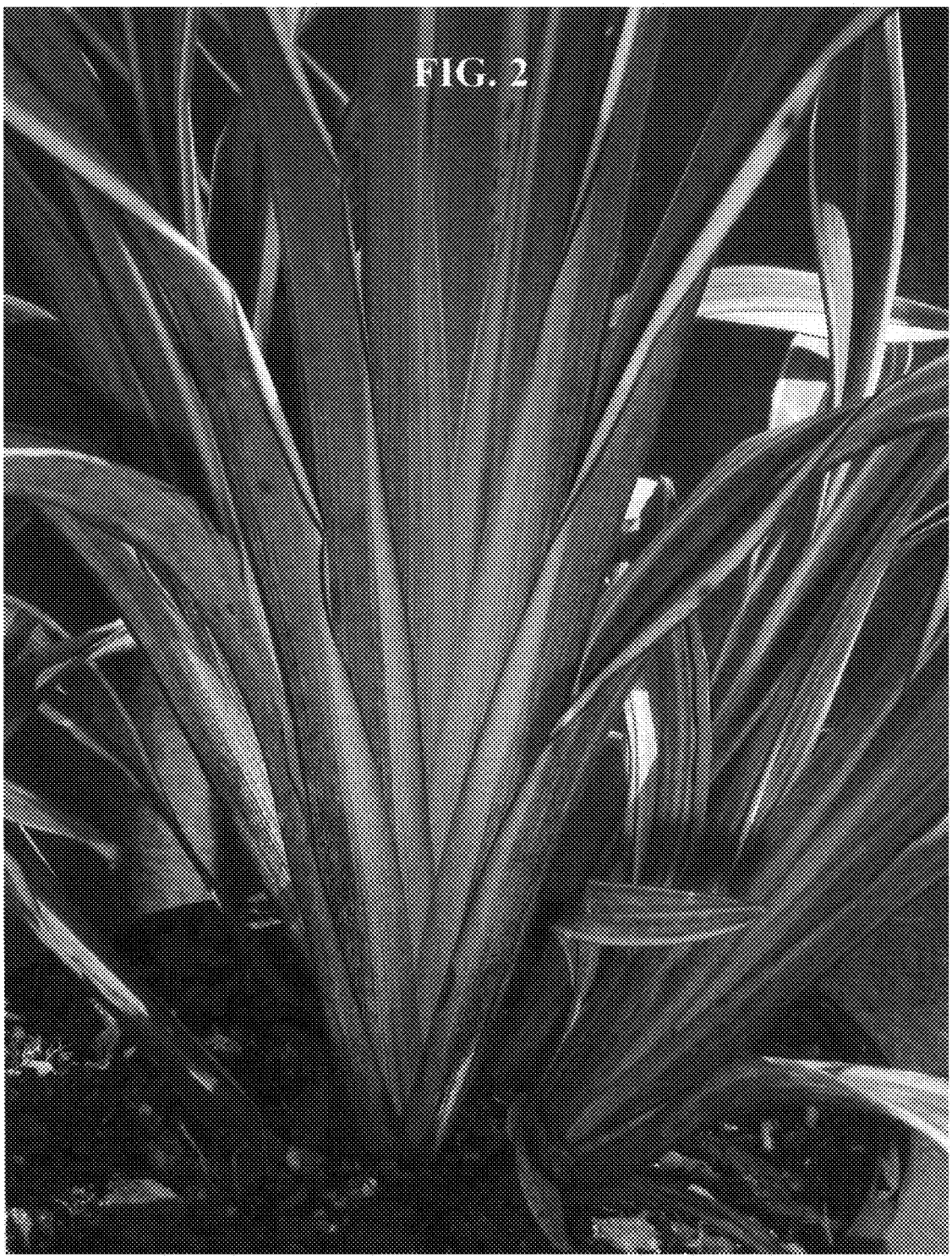
FIG. 2 shows the shoot base detail and arrangement of a *Dianella prunina* 'DPV308' plant at approximately 8-months of age growing in a 140 mm pot.
Figure 3:
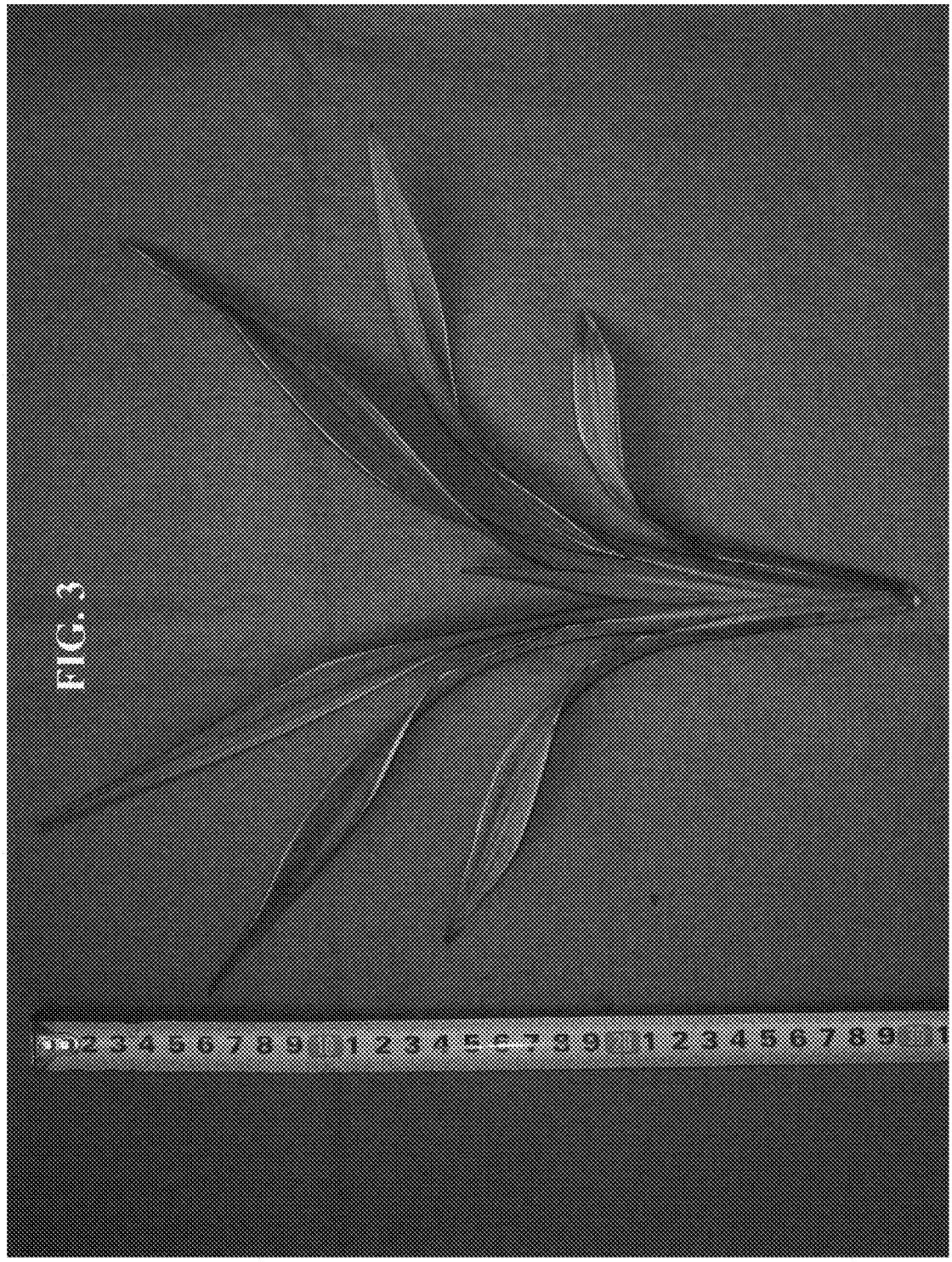
FIG. 3 shows an individual shoot and leaf detail of a *Dianella prunina* 'DPV308' plant at approximately 8-months of age growing in a 140 mm pot.
Figure 4:
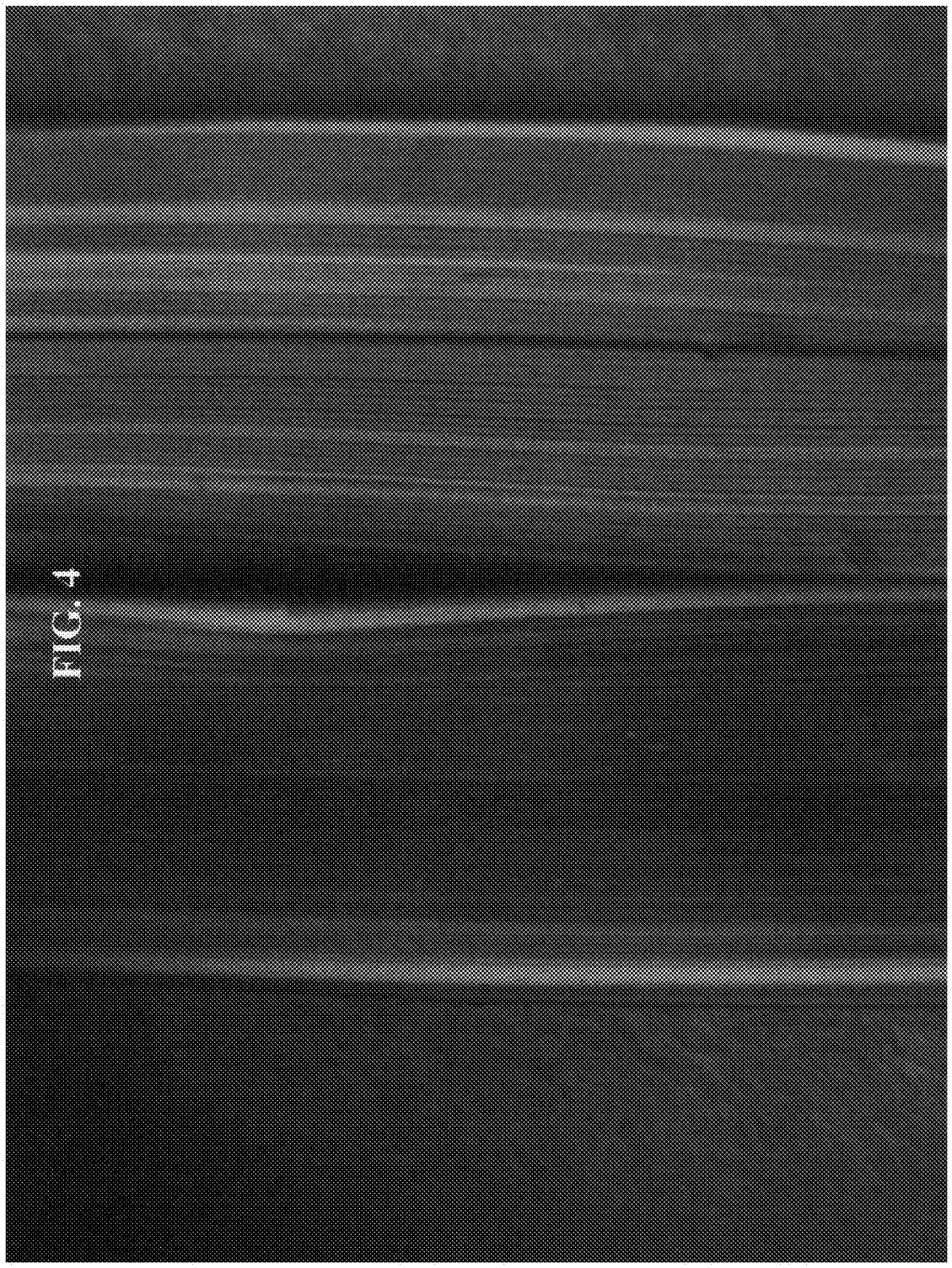
FIG. 4 shows leaf upper side (left) and lower side (right) of a *Dianella prunina* 'DPV308' plant at approximately 8-months of age growing in a 140 mm pot.

These and other features and characteristics of 'DPV308' are apparent from FIGS. 1 to 4.

Comparisons with other *Dianella.*

'DPV308' is a more attractive ornamental grass-like plant as compared with the parent *Dianella prunina.* 'DPV308' is characterized by a combination of an erect and compact plant growth habit with medium density of shoots, short plant height, short internodes and an absence of aerial stems, medium leaf blade width, grayish green leaf color, variegated leaf coloration and strong leaf glaucosity as compared with *Dianella prunina* including the parent variety 'DP303'. The appearance of 'DPV308' is short, compact and with a medium density of shoots with prominent leaf variegation, whereas *Dianella prunina* (common wild form) is tall and sparsely shooting and has no variegation.

*Dianella prunina* 'DP303' (U.S. provisional application No. 60/761,135) is the most similar variety to 'DPV308'. In comparison with 'DP303', cultivar 'DPV308' has prominent leaf variegation with secondary leaf coloration, whereas 'DP303' has no leaf variegation.

That which is claimed is:

1. A new and distinct variety of *Dianella prunina* plant named 'DPV308', substantially as described and illustrated herein.

* * * * *